(12) United States Patent
Vu et al.

(10) Patent No.: US 9,474,586 B2
(45) Date of Patent: Oct. 25, 2016

(54) METHOD FOR PRODUCING A PATIENT-SPECIFIC PAD AND CORRESPONDING PAD

(75) Inventors: Hoang Viet-Ha Julius Vu, Unna (DE); Dirk Wiechmann, Bad Essen (DE)

(73) Assignee: DW Lingual Systems GmbH, Bad Essen (DE)

( * ) Notice: Subject to any disclaimer, the term of this patent is extended or adjusted under 35 U.S.C. 154(b) by 80 days.

(21) Appl. No.: 13/984,479

(22) PCT Filed: Feb. 8, 2012

(86) PCT No.: PCT/EP2012/052150
§ 371 (c)(1),
(2), (4) Date: Aug. 8, 2013

(87) PCT Pub. No.: WO2012/107503
PCT Pub. Date: Aug. 16, 2012

(65) Prior Publication Data
US 2013/0316296 A1 Nov. 28, 2013

(30) Foreign Application Priority Data
Feb. 9, 2011 (DE) .................. 10 2011 003 893

(51) Int. Cl.
*A61C 7/02* (2006.01)
*A61C 7/14* (2006.01)
(Continued)

(52) U.S. Cl.
CPC ................ *A61C 7/02* (2013.01); *A61C 7/146* (2013.01); *A61C 7/16* (2013.01); *A61C 13/0021* (2013.01); *A61C 13/0022* (2013.01)

(58) Field of Classification Search
CPC .......... A61C 7/00; A61C 7/002; A61C 7/02; A61C 7/12–7/16

USPC ...................... 29/896.11; 206/63.5, 368–369
See application file for complete search history.

(56) References Cited

U.S. PATENT DOCUMENTS 2,701,913 A * 2/1955 Lane ................................ 433/16
4,165,561 A * 8/1979 Miller et al. ...................... 433/9
(Continued)

FOREIGN PATENT DOCUMENTS

EP 0 084 443 7/1983
EP 0 502 227 11/1996
(Continued)

OTHER PUBLICATIONS

International Preliminary Report on Patentability and Written Opinion, Aug. 22, 2013, Hoang Viet-Ha Julius Vu.

*Primary Examiner* — Edward Moran
(74) *Attorney, Agent, or Firm* — Greer, Burns & Crain, Ltd.

(57) ABSTRACT

A method for producing at least one patient-specific pad for a modular bracket having a pad and a bracket body includes providing a pad material section. A punch is provided having at least one punching stamp for punching out at least one raw pad from the pad material section. At least one pad is punched out from the pad material section with the punch to produce a raw pad library. A patient-specific set-up is generated. The set-up is made of plaster, and includes the teeth to be treated of an upper jaw and/or of a lower jaw of a patient. A raw pad is selected from the raw pad library for a patient's tooth to be treated. A gap between the raw pad and the corresponding tooth in the set-up is filled using a filling material to produce for the pad a tooth-specific glued surface allowing for a form-fit to the clinical tooth of the patient.

16 Claims, 14 Drawing Sheets

(51) Int. Cl.
*A61C 7/16* (2006.01)
*A61C 13/00* (2006.01)

(56) References Cited

U.S. PATENT DOCUMENTS

| | | |
|---|---|---|
| 5,722,826 A | 3/1998 | Tuneberg et al. |
| 5,827,058 A | 10/1998 | Kelly et al. |
| 5,971,754 A * | 10/1999 | Sondhi et al. .......... 433/24 |
| 5,993,205 A | 11/1999 | Heiser et al. |
| 7,527,147 B2 * | 5/2009 | Corcoran ............ A61C 7/12 206/369 |
| 2002/0010568 A1 | 1/2002 | Rubbert et al. |
| 2002/0058228 A1 | 5/2002 | Andreiko |
| 2003/0224317 A1 | 12/2003 | Andreiko et al. |
| 2006/0223021 A1 | 10/2006 | Cinader, Jr. et al. |
| 2008/0233531 A1 | 9/2008 | Raby et al. |

FOREIGN PATENT DOCUMENTS

| | | |
|---|---|---|
| EP | 0 695 539 | 5/2003 |
| EP | 1 844 730 | 10/2007 |
| EP | 1 941 842 | 7/2008 |
| EP | 1 474 064 | 11/2008 |
| EP | 1 702 582 | 10/2010 |

* cited by examiner

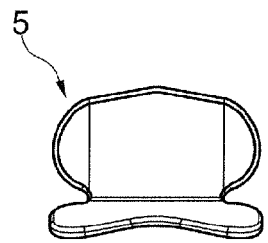
Fig. 3f
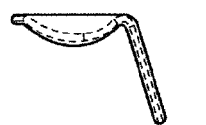 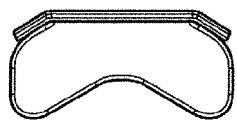 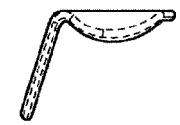 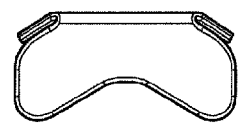
Fig. 3b    Fig. 3c    Fig. 3d    Fig. 3e
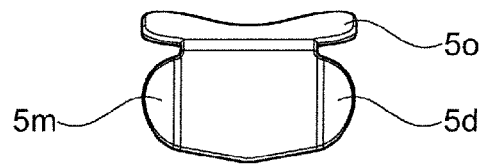
Fig. 3a
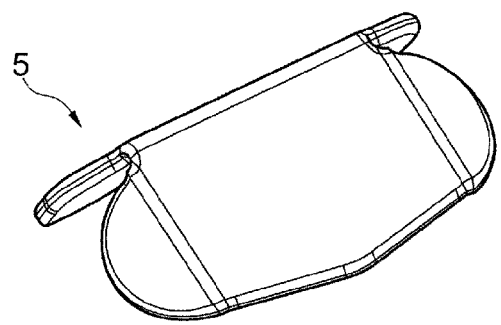
Fig. 3g

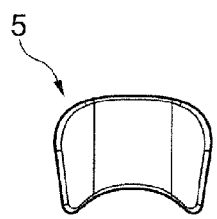
Fig. 4f
         
Fig. 4b      Fig. 4c      Fig. 4d      Fig. 4e
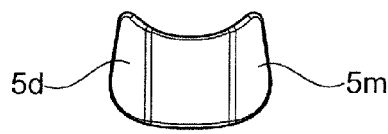
Fig. 4a
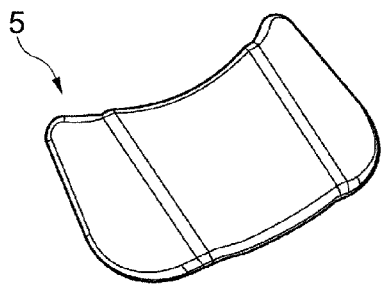
Fig. 4g

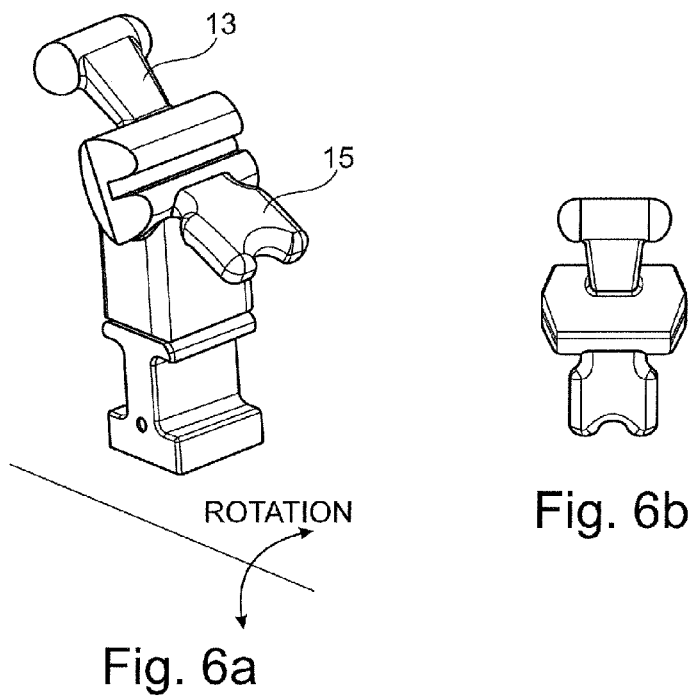
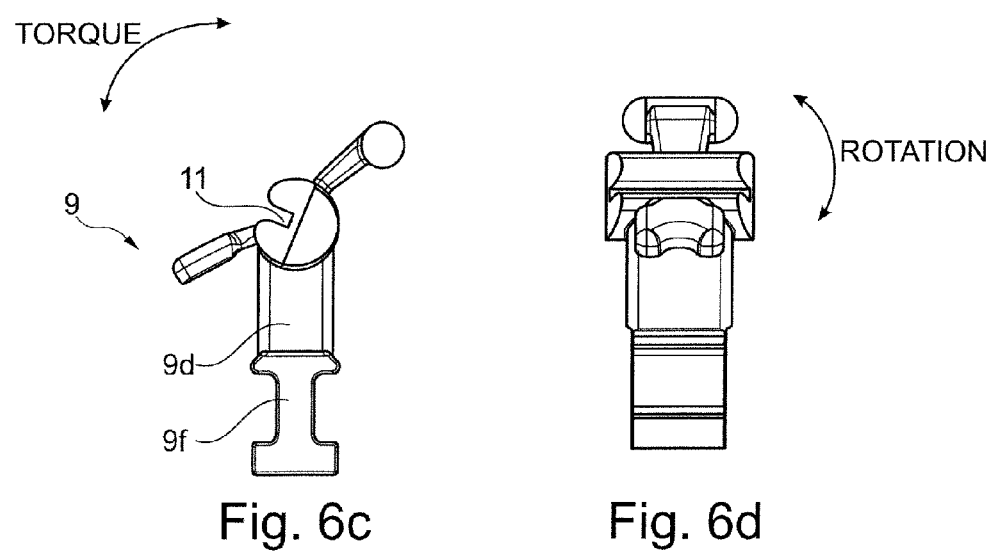

– 1 –
METHOD FOR PRODUCING A PATIENT-SPECIFIC PAD AND CORRESPONDING PAD

PRIORITY CLAIM AND REFERENCE TO RELATED APPLICATION

The application is a 35 U.S.C. §371 application of, and claims priority under 35 U.S.C. §365 and 35 U.S.C. §119 from, PCT/EP12/52150, which was filed on Feb. 8, 2012 and claimed priority from German Application 10 2011 003 893.0, which was filed on Feb. 9, 2012.

The invention concerns a method for producing a patient-specific pad and a corresponding pad.

For the orthodontic treatment of patients having fixed braces, brackets are glued on the teeth of the patient to be treated and connected to one another via an archwire. The brackets present a pad for connection with the tooth and a bracket body, which receives the archwire.

Standard brackets can be used as brackets, which are normalised according to certain standard values and may hence be used for a certain range of patients. There is also the possibility to have brackets manufactured individually for patients as disclosed for instance in EP1474064B1, EP07111572A1, US20020010568A1 and EP08103240.

US 2002/0010568 describes a method for producing patient-specific pads for brackets, wherein a glue is placed onto a bracket body. Following hardening, the glue is adapted to the tooth surface of the patient by milling. Alternately, the pads can be stamped out and be brought into a patient-specific form by milling.

While the manufacture of standard brackets does not raise any problems, the production of completely individualised brackets is quite wasteful. In a variation, individual bracket components such as for instance a hook, a wing, a slot for receiving an arch wire and a pad for setting up on a tooth are available in a computer, which are then assembled to build a virtual bracket, wherein this takes place in a virtual set-up of a patient's denture. The virtual bracket so obtained is transferred to a 3D printer to manufacture a real bracket therewith.

The standard brackets have been perceived as detrimental inasmuch as they do not allow for individualisation for a given patient. The wasteful production has been perceived as detrimental with completely individualised brackets.

The object of the present invention is hence to manufacture a patient-specific bracket body in a simple way.

GENERAL DESCRIPTION OF THE INVENTION

This object is satisfied by a method having the characteristics of the claims and by a pad manufactured according to the method.

The process for the production of a patient-specific pad for a modular bracket having a pad and a bracket body comprises the steps of:
a) providing a pad material section, which preferably is plane,
b) providing a punch having at least one punching stamp for punching out at least one raw pad from the pad material section,
c) punching out of at least one raw pad from the pad material section by means of the punch,
d) providing a patient-specific set-up, in particular made of plaster, of the teeth to be treated of an upper jaw and/or of a lower jaw of a patient,
e) selecting a raw pad from for a patient's tooth to be treated and
f) filling a gap between the raw pad and the corresponding tooth in the set-up using a filling material, especially of plastic, in order to produce a tooth-specific glued surface for the pad which provides for a positive form-fit to the clinical tooth of the patient, preferably with subsequent hardening.

In step c), advantageously several raw pads are stamped out of the raw pad material section, especially identical ones or different ones: For example, only raw pads for a certain tooth can be stamped out. Further, at least two different raw pads can be stamped out, each of which is provided for a certain tooth, e.g. for the tooth 11 and 14.

Also, a raw pad each can be stamped out for all teeth of an upper jaw und/or lower jaw.

Subsequent to the stamping out, the raw pads can further be pre-assembled for adapting them further or more to a specific tooth, preferably in at least one subsequent compression step. Preferably, a raw pad is pre-assembled for each tooth of an upper jaw and/or of a lower jaw.

The pre-assembly preferably comprises an adaptation of the buccal/lingual perimeter contour of the at least one raw pad in order to adapt the perimeter contour of the raw pad to a certain tooth size or tooth form. In this manner, raw pads of different sizes can be produced for a specific tooth.

The pre-assembly can also include a bending of selected sections of a raw pad. For example, mesial and/or distal sections of a raw pad can be bent, to build mesial and/or distal wing sections of the raw pad which encompass the corresponding tooth at least by sections.

The pre-assembly can also include a bending of an occlusal section of a raw pad. When a bracket of this kind is glued to the tooth of a patient, then this occlusal section rests occlusally on the corresponding tooth.

The pre-assembly preferably also comprises the formation of protrusions in a pad, e.g. of lingual/buccal protrusions. In this manner, the raw pad can e.g. be adapted to a lingual concave/convex structure of a certain tooth. In one example, the raw pad for a lingual bracket for the tooth 41 is provided with a buccally extending protrusion in order to adapt it to the concave lingual structure of the tooth 41.

In step a), the pad material section is advantageously generated from a biocompatible metal or a biocompatible alloy, in particular titanium, gold, silver or stainless steel or a cobalt-chrome alloy.

Advantageously, a manual adaptation of the raw pad as selected in step e) to its corresponding tooth in the set-up is made, wherein said adaptation can include an adaptation of the form and/or of the size of the raw pad.

To produce a bracket for every tooth of a patient to be treated, a patient-specific pad is prepared in a set-up for each of these teeth.

Each pad is connected to a bracket body for producing a bracket, especially by bonding or welding.

The brackets produced in this manner are positioned on the teeth in a malocclusion model and a transfer tray is then generated. Preferably, the brackets are arranged with their pad on a tooth surface, on the malocclusion model which shows the dentition out of position and a mass is arranged against the brackets which fixes the brackets in their respective position, which they occupy on a tooth of said dentition.

In order to allow for a quick selection of the raw pads, a raw pad library is advantageously provided having a row of at least 14, preferably 16, raw pad containers, each containing raw pads for one tooth of the upper jaw as well as a further row of at least 14, preferably 16, raw pad containers, each containing raw pads for one tooth of the lower jaw.

Preferably, for at least one tooth a further raw pad container is provided in which are arranged e.g. raw pads of a further size and/or having wing sections and/or having half occlusal sections.

The raw pad containers are preferably arranged in a matrix, especially analogically to the FDI dental notation.

DETAILED DESCRIPTION OF THE INVENTION

Additional characteristics, details and advantages of the invention can be seen in the claims and the following description of preferred embodiments as well as using the drawing. The figures are as follows:

FIGS. 3a-3g show several views of a raw pad for the tooth 27,

FIGS. 4a-4g show several views of a raw pad for the tooth 35,

Figure 1C:
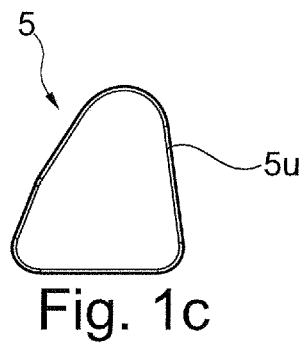
FIGS. 1a-1d show several views of a raw pad for the tooth 21.
Figure 1B:
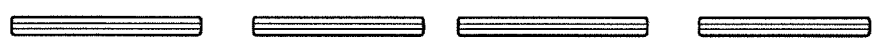
Figure 1A:
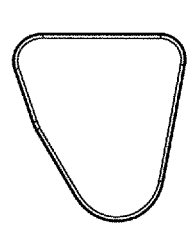
Figure 1D:
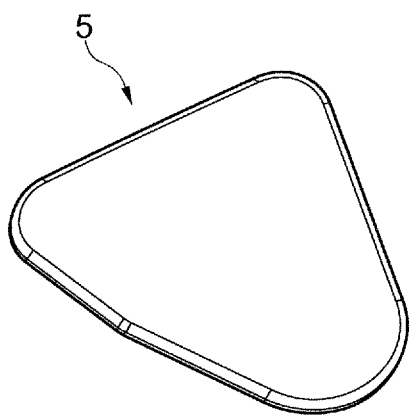
Figure 2C:
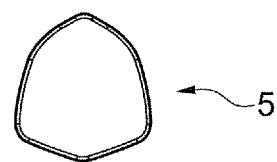
FIGS. 2a-2d show several views of a raw pad for the tooth 23.
Figure 2B:
Figure 2A:
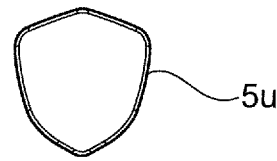
Figure 2D:
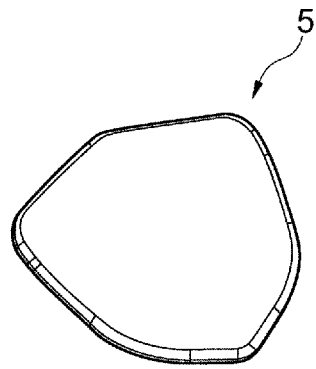
Figure 5F:
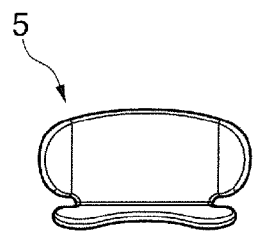
FIGS. 5a-5g show several views of a raw pad for the tooth 37.
Figure 5B:
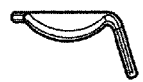
Figure 5C:
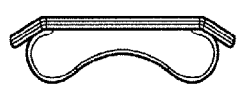
Figure 5D:
Figure 5E:
Figure 5A:
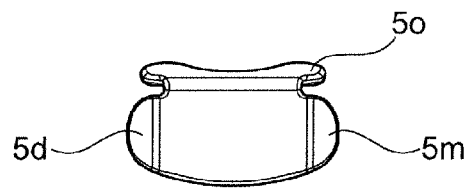
Figure 5G:
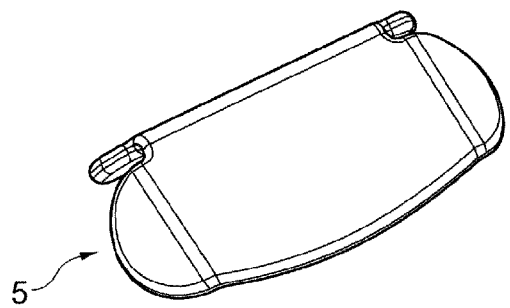
Figure 6E:
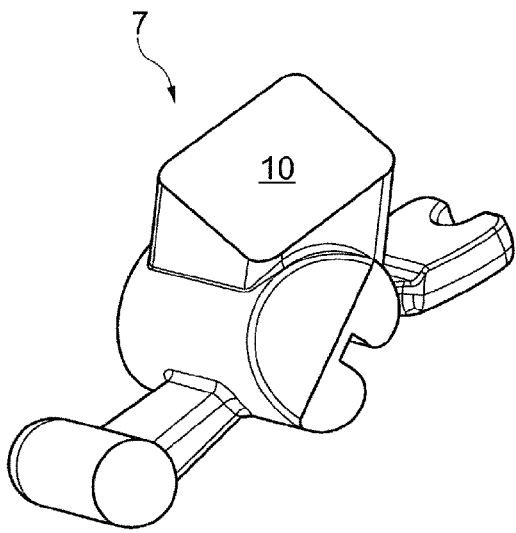
Figure 6F:
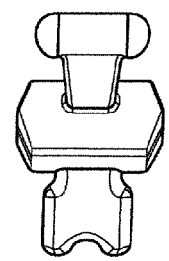
Figure 6G:
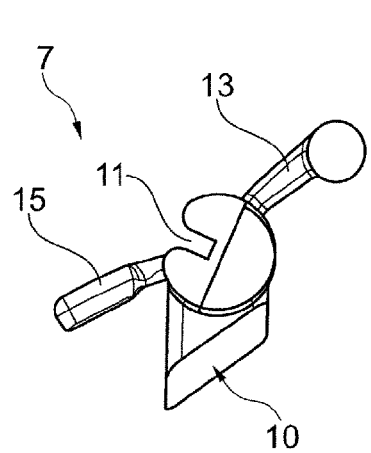
Figure 6H:
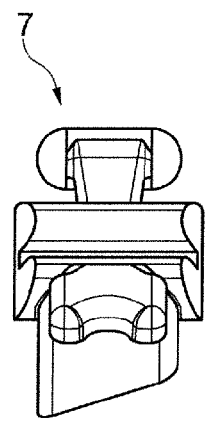
Figure 7A:
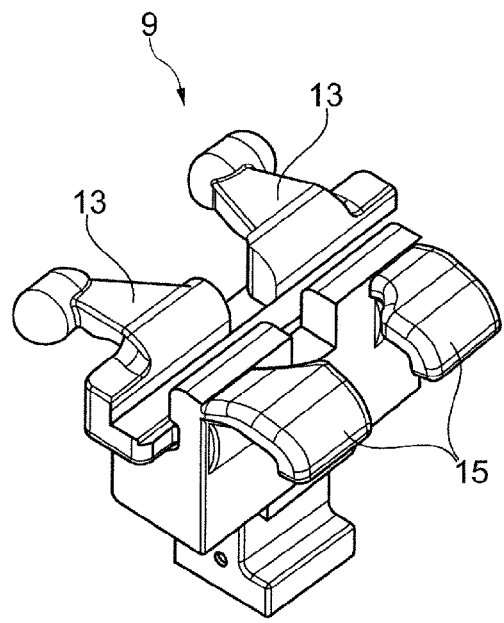
Figure 7B:
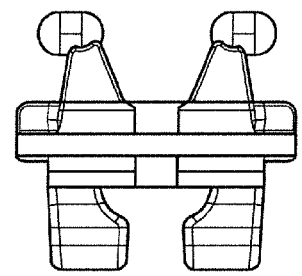
Figure 7C:
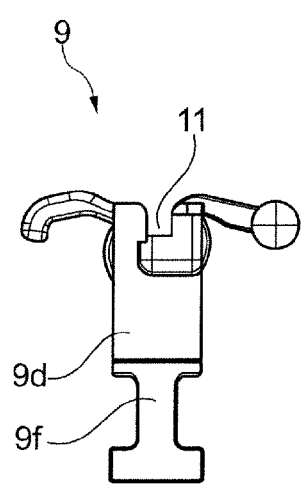
Figure 7D:
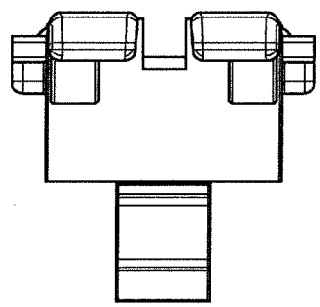
Figures 8A, 8B:
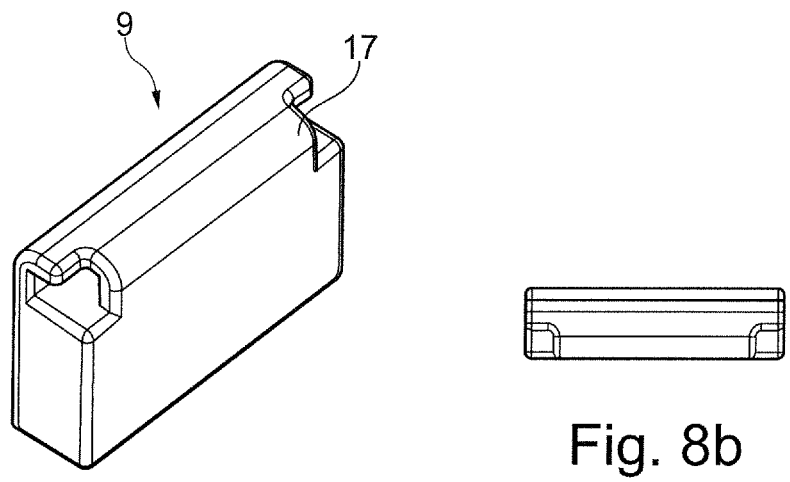
Figures 8C, 8D:
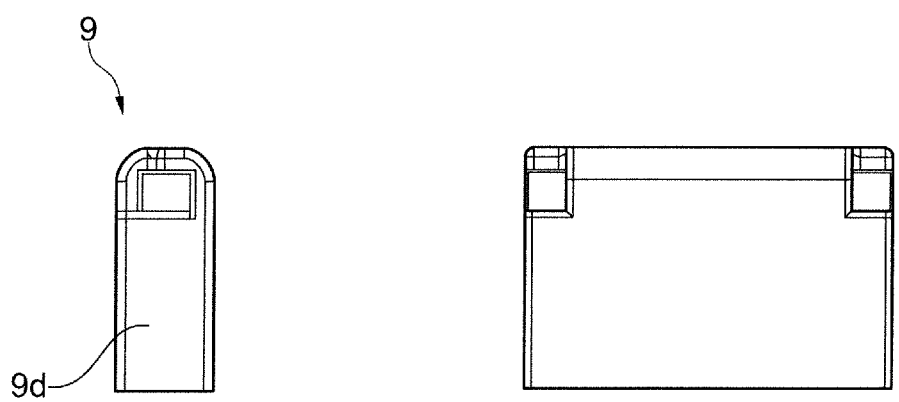
Figure 8E:
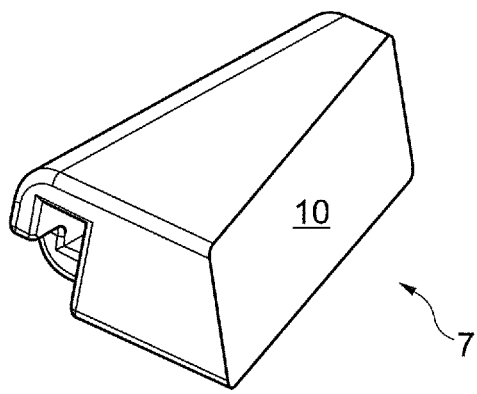
Figure 8F:
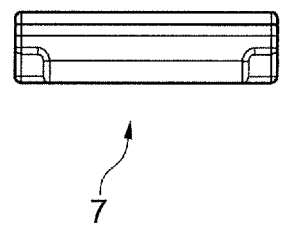
Figure 8G:
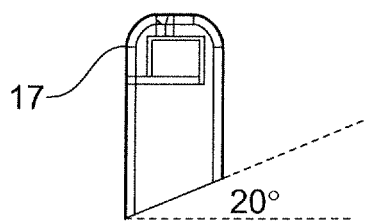
Figure 8H:
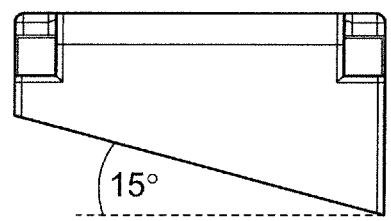
Figure 9:
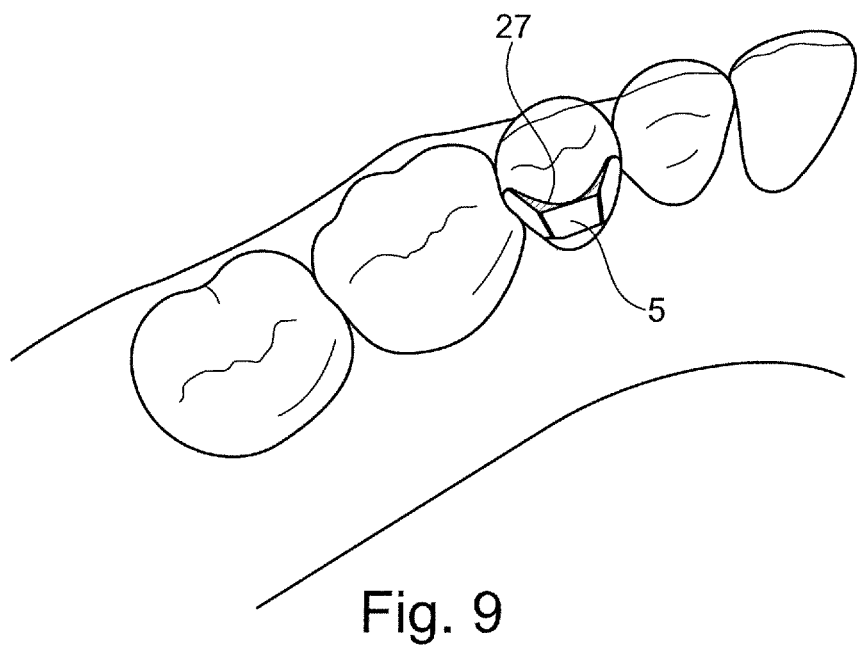
Figures 10A, 10B:
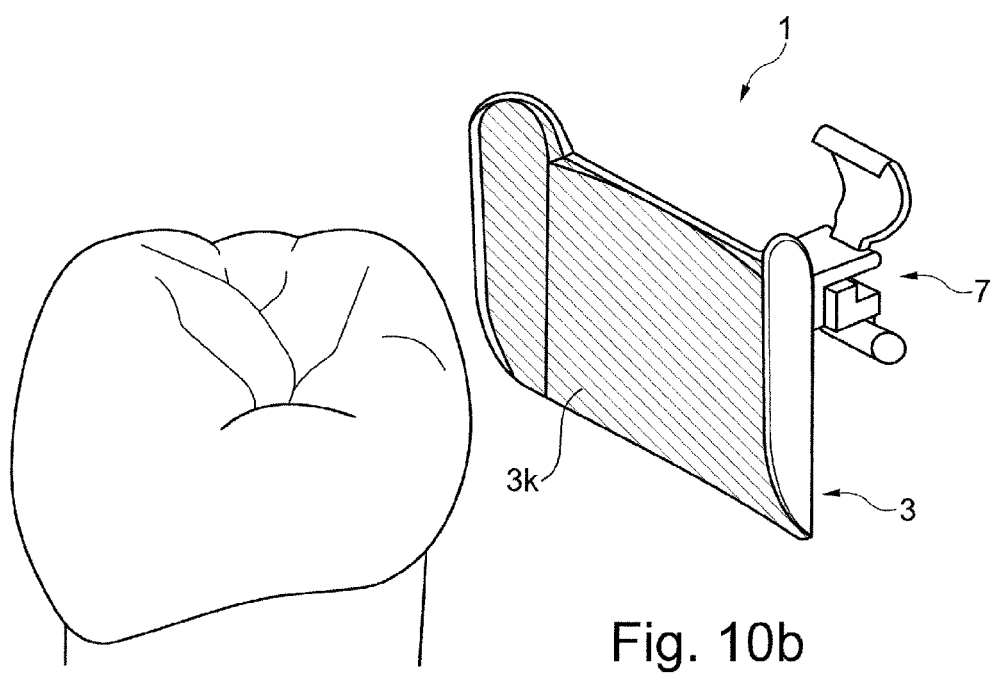
Figure 11:
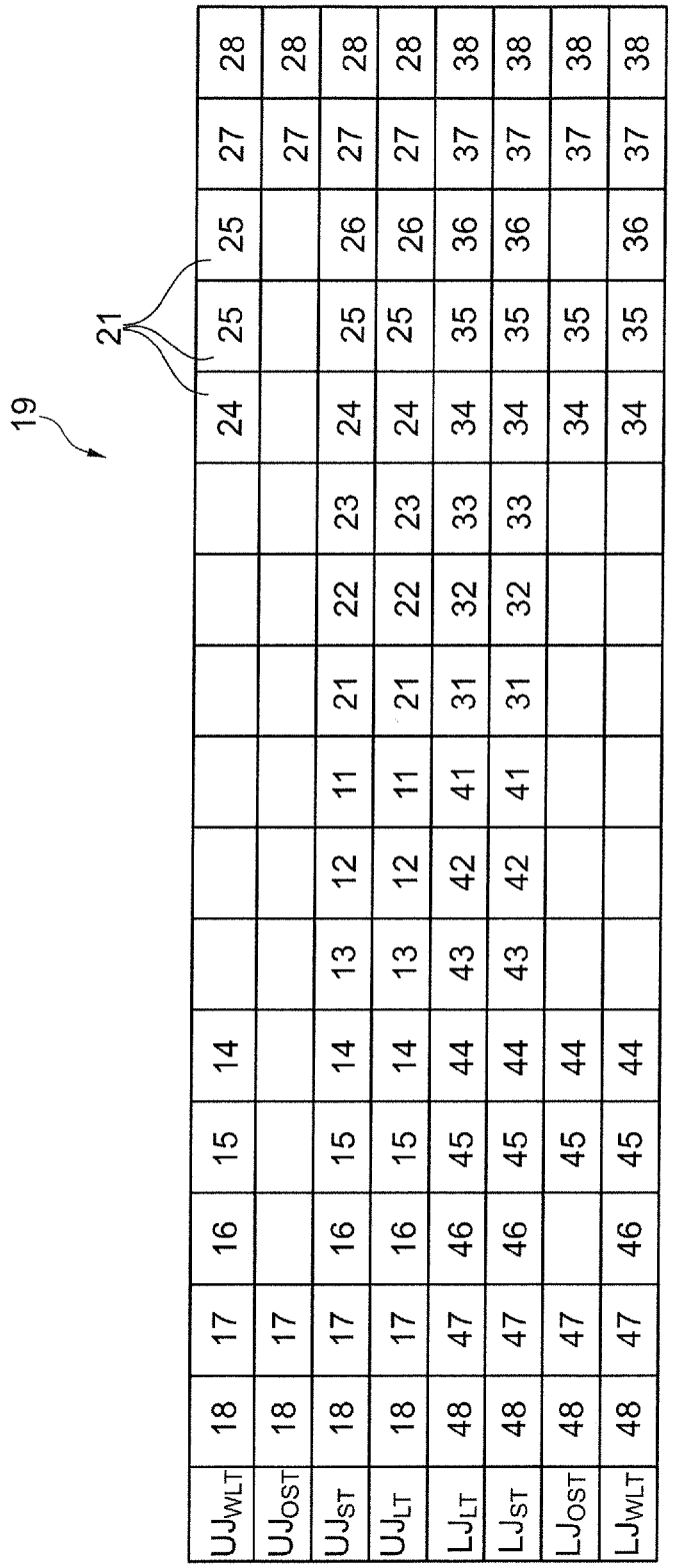
Figure 12:
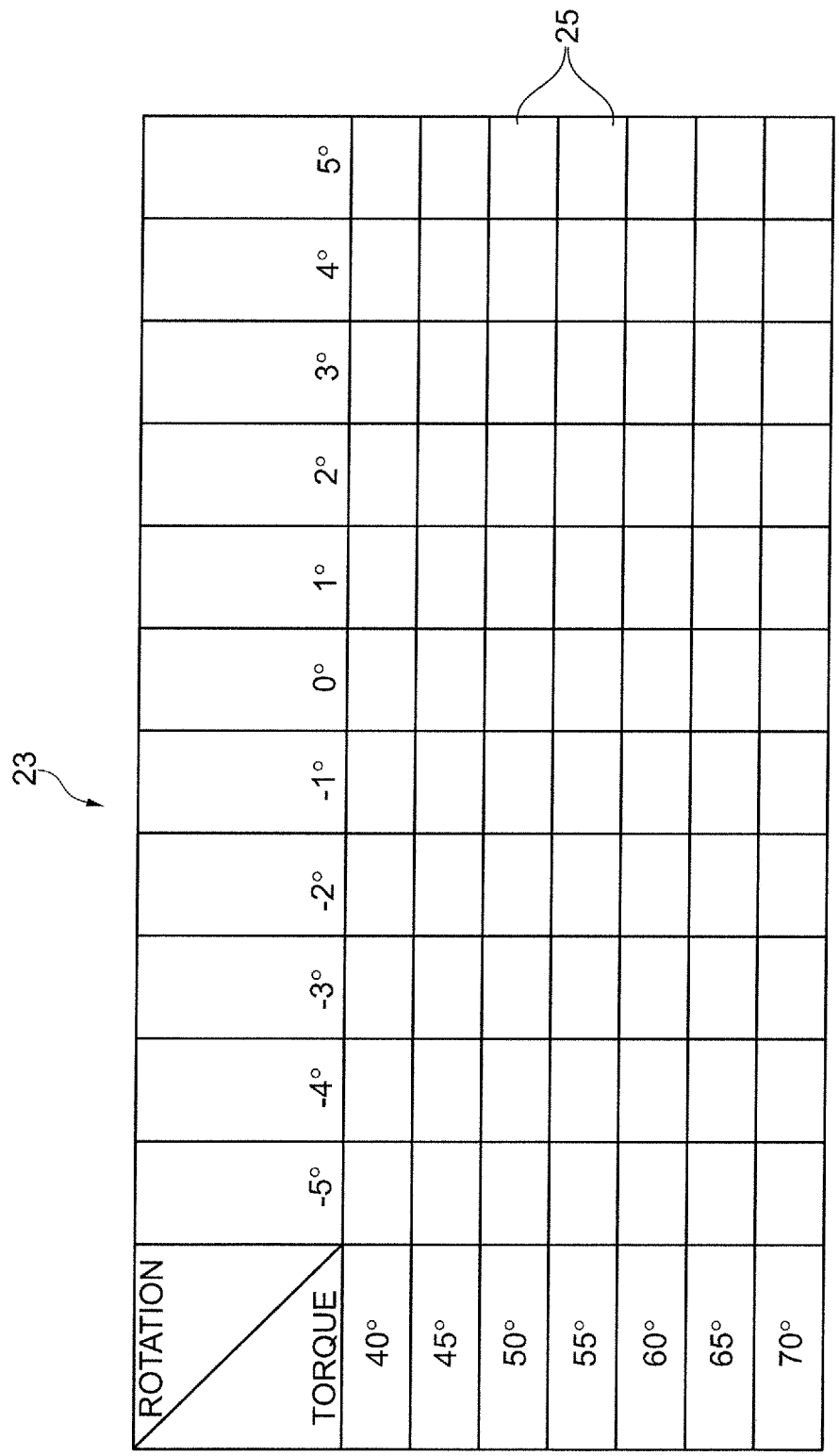

FIGS. 6a-6d show several views of a raw bracket body for the tooth 1 of the upper jaw (UJ 1st), FIGS. 6e-6h show several views of a bracket body, produced from the raw bracket body of FIGS. 6a-6d, FIGS. 7a-7d show several views of a raw bracket body for the UJ or LJ 6th (tooth 6 of the upper jaw or lower jaw), FIGS. 8a-8d show several views of a raw bracket body for the UJ or LJ 7th, FIGS. 8e-8h show several views of a bracket body, produced from the raw bracket body of FIGS. 8a-8d, FIG. 9 shows a perspective view of a target set-up, wherein a raw pad is arranged on a tooth and a gap between both is filled with plastic, FIGS. 10a and 10b show a perspective view of a tooth, on which a finished bracket is introduced, FIG. 11 is a top view on a raw pad library and FIG. 12 is a top view on a bracket body library.

First of all, there are provided a band of material for pads (100 m long, 5 cm wide and 0.4 mm thick) made of stainless steel as well as a punch with a punching stamp, to punch out raw pads out of the pad material band using the punch. The punch punches out several identical raw pads from an inlaid pad material section of the pad material band, wherein the buccal/lingual perimeter contour of the same is adapted to the tooth for which the raw pad is produced. Instead of a pad material band, it is alternately possible also to use a sheet of pad material.

In FIGS. 1a-1d, the six side views as well as a perspective view of a raw pad 5 for the tooth 21 are shown, which was produced that way. The raw pad 5 is flat and presents a constant material thickness over the whole area. The buccal/lingual perimeter contour 5U presents practically the form of a triangle which enables the raw pad 5 being adapted correctly to the tooth 21. The edges of the buccal/lingual perimeter contour 5U, which were generated when punching out, were eliminated in a subsequent compression step, which produces the rounded lateral surfaces of said perimeter contour 5U.

Analogically, FIGS. 2a-2d show a raw pad 5 produced according to the same method for the tooth 23, whereas said raw pad 5 differentiates itself from that of FIG. 1 exclusively through the other form of the buccal/lingual perimeter contour 5U.

FIGS. 3a-3g show the six side views as well as a perspective view of a raw pad 5 for the tooth 27. The raw pad 5 was produced following the same method, as described with reference to FIGS. 1 and 2, still two additional bending steps were however carried out. In a first bending step, a mesial 5m and a distal 5d wing section was formed by folding it over in a press with an appropriate bending tool. In a second bending step, an occlusal section 5o of the raw pad 5 was formed in a press with an appropriate bending tool. This occlusal section 5o rests occlusally on the tooth 27 in the status inserted in the patient.

FIGS. 4a-4d show the six side views as well as a perspective view of a raw pad 5 for the tooth 35. The raw pad 5 was produced following the same method, as described with reference to FIGS. 1 and 2, a mesial 5m and a distal 5d wing section was however formed in a further bending step.

FIGS. 5a-5g show the six side views as well as a perspective view of a raw pad 5 for the tooth 37. The raw pad 5 was produced following the same method, as described with reference to FIGS. 1 and 2, still two additional bending steps were however carried out, as described previously with reference to FIG. 3: In a first bending step, a mesial 5m and a distal 5d wing section was formed by folding it over in a press with an appropriate bending tool. In a second bending step, an occlusal section 5o of the raw pad 5 was formed in a press with an appropriate bending tool. This occlusal section 5o rests occlusally on the tooth 37 in the status inserted in the patient.

The raw pads 5 obtained that way were sorted into a raw pad library 19 which is represented on FIG. 11. The raw pad library 19 comprises 16 times 8 raw pad containers 21, which are arranged in a matrix pattern. In the row $UJ_{LT}$ and $LJ_{LT}$ are respectively 16 raw pad containers 21, that is to say that a raw pad container 21 is provided for every tooth of the upper jaw and of the lower jaw. The raw pad containers 21 are arranged analogically to the FDI dental notation in the dentistry: from the 8th left starting over the 1st to the right up to the 8th of the other half of the face. Accordingly, the raw pad containers are designated as 18 via 11 and 21 to 28, respectively as 48 via 41 and 31 to 38. Raw pads 5 belonging to or being adapted to the respective tooth are situated in each of said raw pad containers 21.

The row $UJ_{LT}$ and $LJ_{LT}$ contains the raw pads 5 for the upper jaw respectively the lower jaw with large teeth. The row $UJ_{ST}$ and $LJ_{ST}$ contains the raw pads 5 for the upper jaw respectively the lower jaw with small teeth. The row $UJ_{OST}$ and $LJ_{OST}$ contains the raw pads 5 with occlusal sections 5o for the upper jaw respectively the lower jaw with small teeth, in this instance only for the teeth 17, 18, 28, 27 as well as 34, 35, 37, 38, 44, 45, 47 and 48. In the row $UJ_{WLT}$ and $LJ_{WLT}$ there are contained the raw pads 5 with wing sections 5m, 5d for the upper jaw respectively the lower jaw with large teeth, in this instance only for the teeth 14, 15, 16, 17, 18, 24, 25, 26, 27, 28 as well as 34, 35, 36, 37, 38, 44, 45, 46, 47 and 48.

To obtain now a patient-specific pad, the procedure is as follows: An impression of an upper jaw and lower jaw of a patient respectively is taken and a plaster model is prepared by using the former. The plaster models are mounted respectively arranged into an articulator which mirrors the relative position of the jaws relative to one another (malocclusion models). The target set-up is completed from said malocclusion model which depicts the planned situation at the end of the treatment. To prepare it, the teeth are cut out individually from the malocclusion models of the patient and then re-assembled in the target situation to reach, thereby producing the target set-up.

A suitable raw pad 5 respectively for the teeth to be treated is taken from the raw pad library 19. The taken raw pads 5 are further adapted onto the corresponding teeth of the plaster model (target set-up) possibly by hand, wherein consequently the form and/or the size can be adapted, but bendings can still be carried out manually. Subsequently, the raw pads 5 are respectively held on the corresponding tooth in the target set-up and a gap 27 between the tooth and the raw pad 5 is filled with a filling material made of plastic, as shown in FIG. 9. In this manner, the raw pad 5 is given a patient-specific glued surface 3K and thus becomes a pad 3. This patient-specific glued surface 3K can later be laid onto the tooth of the patient in a form locking manner and then be fixedly connected thereto using a glue.

The patient-specific pads 3 obtained that way are subsequently connected respectively to a patient-specific bracket body 7 which is taken from a bracket body library 23 which is built analogically to the raw pad library, described as follows.

FIGS. 6a-6d show different views of a raw bracket body 9 for an UJ 1st, wherein said presents a fixing section 9f, a spacer section 9d, a slot 11, a hook 13 and a wing 15. FIGS. 6e-h show the cut surface 10, which is arranged according to the three parameters.

FIGS. 7a-7d show different views of a raw bracket body 9 for an UJ or a LJ 6th, that also presents a fixing section 9f, a spacer section 9d, a slot 11, two hooks 13 and two wings 15.

FIGS. 8a-8d show different views of a raw bracket body 9 in the form of a little tube 17 for an UJ or a LJ 7th, that also presents a spacer section 9d.

The raw bracket bodies 9 were produced in a metal injection moulding (MIM) process (alternately in a selective laser melting process) and consist of a cobalt-chrome alloy (alternately for instance made of stainless steel). The hooks 13 and wings 15 respectively present a material tapering on their end facing the slot 11, so that they can be bent respectively manually into a suitable angular position around the slot 11.

To make an optimal slot 11 available for the treatment the raw bracket bodies 9 of the FIGS. 6 and 7 are fastened to a carrier with their fixing sections 9f. Approx. 100 pieces can be fixed to the carrier. The carrier with the raw bracket bodies 9 is dipped into a suitable liquid bath in which the slot 11 of every single raw bracket body 9 is trimmed by means of a wire erosion procedure. This operation may also involve several passes (for planing) The result is a very precise slot 11 with a minimal margin of error with respect to the norm.

The raw bracket body of FIGS. 8a-8d has no fixing section, because it has no slot which must be produced extremely precisely for the treatment.

After this step, the raw bracket bodies 9 of the FIGS. 6 to 8 are fixed with their slot side end in a corresponding negative form (to this end), whereas alternately a fastening is possible on the opposite end. The spacer section 9d of the respective raw bracket bodies 9 is cut through with various angles using a saw. Three parameters can be set during the cutting-through phase:

The first parameter is a distance of the resulting cut surface of the spacer section 11. The smaller this distance can be selected, the less a patient can feel the bracket.

The second parameter is an angle about the longitudinal axis of the slot 11 (mesio-distal axis). According to the deviation of the cutting angle from an average default value, the torque applied is more or less important, see FIGS. 6a, 6c and 6d for nomenclature.

The third parameter is an angle with respect to a vertical line towards the longitudinal axis of the raw bracket body 9 (occlusal-gingival axis). According to the deviation of the cutting angle from an average default value, the rotation applied is more or less important, see FIGS. 6a, 6c and 6d for nomenclature.

For a raw bracket body 9, these three parameters are now established and the spacer section 9d is cut through accordingly with a saw, whereby a bracket body 7 is produced. FIGS. 6e-6h show the raw bracket body 9 of FIGS. 6a-6d, at which the spacer section in terms of torque at 55° and in terms of rotation at 15° was cut through, whereby the bracket body 7 of FIGS. 6a-6d is produced. FIGS. 8e-8h show the raw bracket body 9 of FIGS. 8a-8d, at which the spacer section in terms of torque at 20° and in terms of rotation at 15°, respectively, was cut through.

The bracket bodies 7 obtained in this manner are sorted into bracket body containers 25 of a bracket body library 23 (FIG. 12), wherein respectively a bracket body library is available for each raw bracket body 9 of the FIGS. 6a-6d, 7a-7d and 8a-8d. In other words, the raw bracket body 9 of FIGS. 6a-6d has its own bracket body library, just like that of FIGS. 7a-7d and 8a-8d.

FIG. 12 shows a bracket body library 23, which is built analogically to the raw pad library and is filled with bracket bodies 7. The bracket bodies 7 are divided in 1° steps in terms of rotation of −5° to +5° and in terms of torque divided into 5° steps from 40° to 70°. Naturally, other interval limits as well as other interval steps can here be used, in particular also depending on the raw bracket body 9, i.e. for the raw bracket body 9 of FIGS. 6a-6d other interval limits and other interval steps can be used as for that of FIGS. 7a-7d. The bracket bodies 7 along with the pad 3 form a finished bracket 1.

The method of production of a patient-specific bracket continues as follows: A patient-specific pad 3 is already fixed to the teeth to be treated in the set-up. For every pad 3, a suitable bracket body 7 is now taken from the bracket body library and glued fixedly to its respective pad 3. The bracket bodies 7 are advantageously guided to the respective pad 3 via a "mechanical finger" and then glued fixedly thereto.

A 2D-scan of the UJ model and/or LJ model is taken from the bracket set-up obtained that manner from the corresponding cranial respectively caudal direction (elevation view), so as to bend a corresponding archwire using a wire bending machine using these data.

Subsequently, the plaster models are soaked in a water bath which enables to release the pads with the bracket bodies fixedly glued thereto, which then are welded fixedly to one another using a laser.

The brackets 1 produced in that manner are placed on a plaster model of the patient (malocclusion model), see FIGS. 10a and 10b, and there fixed, to produce a transfer tray, for example made of silicone, preferably by arranging a hardening mass, preferably on the basis of silicone, onto the brackets 1 arranged on the malocclusion model.

A raw pad 5 each was represented respectively in FIGS. 1s to 5g for the teeth 21, 23, 27, 35 and 37. It is generally possible, to develop for every tooth of the upper and/or lower jaw respectively a raw pad 5 adapted especially to this tooth. Alternately, it is possible to use a raw pad 5 for several teeth, for instance a raw pad 5 for the teeth 32, 31, 41 and 42.

The raw pad library 19 according to FIG. 11 in each row comprises 16 raw pad containers 21, in which raw pads 5 are arranged respectively for a tooth. Consequently, raw pads 5 are respectively provided from the 8th of the one side to the 8th of the other side. The raw pad library 19 in an alternative embodiment in each row comprises 14 raw pad containers 21 in which raw pads 5 are respectively arranged for one tooth (from the 7th to the 7th). Consequently, raw pads 5 are respectively provided from the 7th of the one side to the 7th of the other side.

In the context of the present invention, by matrix-like arrangement is meant an arrangement in lines and columns.

The bracket body library 23 comprises bracket body containers 25 with bracket bodies 7 arranged therein. The bracket body containers 25 respectively the bracket bodies 7 arranged therein are hence sorted per parameter values of the three parameters (distance between cut surface and slot, angle of mesial-distal axis, angle of occlusal-gingival axis). It is generally possible to vary all three parameters in a bracket body library 23 of a bracket body 9. It is hence for instance possible again to produce the bracket body library 23 of FIG. 12 with the same values for torque and rotation, whereas however the third parameter (the distance between cut surface and slot) is varied, for instance enlarged or reduced by 1 mm. That way, there would be twice the bracket body library 23 of FIG. 12: once with a larger distance and once with a smaller distance, through which a new bracket body library 23 is built. The matrix-like arrangement of FIG. 12 is hence extended into the third dimension, in which the additional parameter is varied. This general version is in practice as a rule not necessary: Since the distance between cut surface and slot should always be as small as possible so that the generated bracket 1 disturbs the patients as little as possible, the bracket body library 23 of FIG. 12 can be sufficient, with which the distance between cut surface and slot is as small as possible.

Generally, an advantageous method for producing a patient-specific bracket body 7 comprises the following steps:
a) providing a raw bracket body 9 having a spacer section 9d,
b) establishing a first parameter for cutting through the spacer section 9d, a distance of a resulting cut surface of the spacer section 9d from the slot 11 in order to establish a suitable height of the bracket body 7,
c) establishing a second parameter for cutting through the spacer section 9d, a cutting angle to a mesio-distal axis, in order to establish a suitable torque value of the bracket body 7,
d) establishing a third parameter for cutting through the spacer section 9d, a cutting angle to an occlusal-gingival axis in order to establish a suitable rotation value of the bracket body 7,
e) cutting through the spacer section 9d according to the three established parameters, whereby a bracket body is produced.

The raw bracket body 9 is preferably manufactured in step a) by a MIM process or a selective laser melting process and/or is generated from a biocompatible metal or a biocompatible alloy, in particular titanium, gold, silver or stainless steel or a cobalt-chrome alloy.

Advantageously, the cutting through in step e) occurs by means of a saw.

Establishing the three parameters in steps b) to d) in a variant occurs individually for a patient.

In another variant, the parameters in steps b) to d) are each varied in a selected interval with selected interval steps in order to generate a bracket body library 23, wherein bracket bodies 7 are arranged with their respective differing parameter values.

Preferably, the raw bracket bodies 7 of a bracket body library 23 of one raw bracket body 9 with bracket body containers 25 for accommodating bracket bodies 7 are produced, wherein the bracket body containers 25 are arranged in a matrix pattern. Bracket bodies 7 are arranged in the bracket body containers 25. The bracket bodies 7 are advantageously arranged in the bracket body containers 25, sorted line-by-line according to one parameter and column-by-column according to another parameter. Both the parameters are preferably varied respectively within selected interval limits with selected interval steps.

Advantageously, one of the parameters is the third or the second parameter and the other parameter is the second or the third parameter.

An advantageous method for producing a patient-specific bracket having a patient-specific pad and a patient-specific bracket body can hence be divided into the following steps:
1. Production of a raw pad library:
providing a preferably flat section of pad material,
providing a punch with at least one punching stamp for punching out tooth-specific raw pads out of the section of pad material,
punching out the tooth-specific raw pads out of the section of pad material using the punch,
optional pre-assembly of the raw pads.
2. Production of a bracket body library:
providing raw bracket bodies having a spacer section,
optionally providing highly precise slots in the raw bracket bodies (for instance with wire erosion),
division of the spacer sections with selected parameter values for the three parameters
3. Generating a patient-specific target set-up, in particular made of plaster, of the upper jaw and/or lower of a patient to be treated.
4. Selection of a raw pad from the raw pad library for a patient's tooth to be treated.
5. Filling a gap between the raw pad and the corresponding tooth in the target set-up with a filling material, in particular made of plastic, to obtain a tooth-specific glued surface for the pad, which enables a positive locking with the clinical tooth of the patient.
6. Selection of a bracket body from the bracket body library for each pad.
7. Fixing the bracket body on the pad, to build the patient-specific bracket.

The method steps need not however be carried out in that order. It is hence for instance possible, alternatively to first connect the raw pads 5 with their corresponding bracket bodies 7 and to build the glued surface 3K only subsequently.

LIST OF REFERENCE NUMERALS 1 bracket
3 pad
3K glued surface of the pad
5 raw pad
5m mesial (wing) section of a raw pad
5d distal (wing) section of a raw pad
5o occlusal (wing) section of a raw pad
5U buccal/lingual perimeter contour
7 bracket body
9 raw bracket body
9d spacer section of the raw bracket body 9f fixing section of the raw bracket body
10 cut surface
11 slot
13 hook
15 wing
17 little tube
19 raw pad library
21 raw pad container
23 bracket body library
25 bracket body container
27 gap

The invention claimed is:

1. A method for producing at least one patient-specific pad for a modular bracket having a pad and a bracket body comprising:
   a) providing a pad material section,
   b) providing a punch having at least one punching stamp for punching out a plurality of raw pads from the pad material section,
   c) punching out the plurality of raw pads from the pad material section by means of the punch,
   d) providing a set of containers comprising a first row of at least 14 raw pad containers, a second row of at least 14 raw pad containers, and at least one additional raw pad container,
   e) placing the plurality of raw pads in the set of containers such that each of the raw pad containers of the first row contains raw pads for one tooth of the upper jaw, each of the raw pad containers of the second row contains raw pads for one tooth of the lower jaw, and the at least one additional raw pad container contains raw pads of a further size and/or with wing sections and/or with half occlusal sections, thereby forming a raw pad library,
   f) generating a patient-specific target set-up, in particular made of plaster, of the teeth to be treated of an upper jaw and/or of a lower jaw of a patient,
   g) selecting a raw pad from the raw pad library for a patient's tooth to be treated, and
   h) filling a gap between the raw pad and the corresponding tooth in the target set-up using a plastic filling material in order to produce for the pad a tooth-specific glued surface allowing for a form-fit to the clinical tooth of the patient.

2. The method according to claim 1, wherein in step c) more than two raw pads are stamped out of the pad material section.

3. The method according to claim 2, wherein for all teeth of an upper jaw and/or lower jaw one raw pad each is stamped out.

4. The method according to claim 1, wherein the plastic filling material hardens in a form having positive fit to a tooth of the target set-up on the surface opposite the raw pad.

5. The method according to claim 1 wherein subsequent to step c) the plurality of raw pads are pre-assembled to specific teeth.

6. The method according to claim 5, wherein the pre-assembly comprises an adaptation of the buccal/lingual perimeter contour of the plurality of raw pads in order to adapt this perimeter contour of each of the plurality of raw pads to a certain tooth size or tooth form.

7. The method according claim 5, wherein the pre-assembly includes a bending of selected sections of at least one of the plurality of raw pads to build mesial and/or distal wing sections of the raw pad which encompass the corresponding tooth at least by sections.

8. The method according to claim 5, wherein the pre-assembly includes a bending of an occlusal section of at least one of the plurality of raw pads, which section then rests occlusally on the corresponding tooth.

9. The method according to claim 5, wherein the pre-assembly includes the formation of lingual/buccal protrusions on at least one of the plurality of raw pads.

10. The method according to claim 1, wherein the pad material section is formed of a biocompatible metal or a biocompatible alloy.

11. The method according to claim 1, wherein a manual adaptation of the raw pad selected in step g) to its corresponding tooth is made, wherein said adaptation includes an adaptation of the form and/or of the size of the raw pad.

12. The method according to claim 11, wherein for each tooth to be treated of a patient, a pad is produced in the target set-up.

13. The method according to claim 12, comprising connecting each pad to a bracket body for producing a bracket, by gluing or welding.

14. The method according to claim 13, wherein the brackets are respectively positioned on the teeth in a malocclusion model and then a transfer tray is obtained by arranging a hardening mass onto the brackets which are positioned in the malocclusion model.

15. The method according to claim 1, wherein the raw pad material section comprises a plane.

16. The method according to claim 10, wherein the biocompatible metal or a biocompatible alloy comprises titanium, gold, silver or stainless steel or a cobalt-chrome alloy.

* * * * *